US00PP26364P3

(12) United States Plant Patent
Gray et al.

(10) Patent No.: US PP26,364 P3
(45) Date of Patent: Feb. 2, 2016

(54) *ROSA* PLANT NAMED 'GRAPPL'

(50) Latin Name: ***Rosa* hybrid**
Varietal Denomination: GRAppl

(71) Applicants: John Gray, Highfields (AU); Sylvia E. Gray, Highfields (AU)

(72) Inventors: John Gray, Highfields (AU); Sylvia E. Gray, Highfields (AU)

( * ) Notice: Subject to any disclaimer, the term of this patent is extended or adjusted under 35 U.S.C. 154(b) by 81 days.

(21) Appl. No.: 14/120,562

(22) Filed: Jun. 2, 2014

(65) Prior Publication Data

US 2015/0351296 P1 Dec. 3, 2015

(51) Int. Cl.
*A01H 5/02* (2006.01)

(52) U.S. Cl.
USPC ..... Plt./102

(58) Field of Classification Search
USPC ..... Plt./102
CPC ..... A01H 5/0222; A01H 5/0216
See application file for complete search history.

*Primary Examiner* — Kent L Bell
(74) *Attorney, Agent, or Firm* — Cassandra Bright

(57) ABSTRACT

A new and distinct floribunda type *Rosa* hybrid named 'GRAppl' is disclosed, characterized by complete resistance to *Diplocarpon rosae* and strong tolerance for powdery mildew. Plants produce dark red-purple flowers with a strong fragrance and are typically dense and twiggy, reaching a height of between 1 to 1.2 meters. The new cultivar is a *Rosa* typically suited for ornamental container and landscape use.

2 Drawing Sheets

Figure 1:
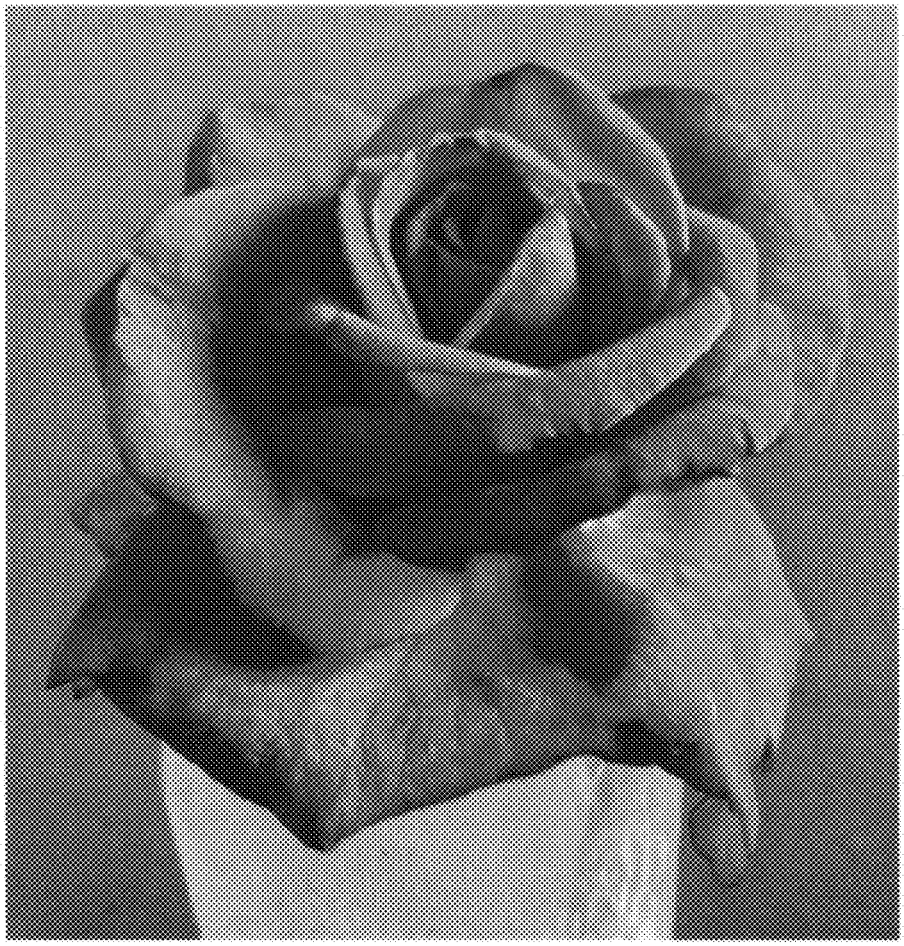

Latin name of the genus and species: *Rosa* hybrid.
Variety denomination: 'GRAppl'.

BACKGROUND OF THE INVENTION

The new cultivar is the result of a planned breeder program, conducted by the inventors, John Gray and Sylvia Gray, citizens of Australia. The new variety resulted from the crossing of a proprietary, unpatented, unnamed seedling with the pollen parent *Rosa* 'GRAsuper' U.S. Plant Pat. No. 23,175. The crossing was made Dec. 12, 2011. The discovery was made Mar. 12, 2012.

After selecting the new cultivar, asexual reproduction of 'GRAppl' was first performed in the same commercial nursery by vegetative cuttings Mar. 30, 2012. 'GRAppl' has since produced two generations and has shown that the unique features of this cultivar are stable and reproduced true to type.

SUMMARY OF THE INVENTION

The cultivar 'GRAppl' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GRAppl'. These characteristics in combination distinguish 'GRAppl' as a new and distinct *Rosa* hybrid cultivar:

1. Complete resistance to the fungus *Diplocarpon rosae.*
2. Strong perfume scent to flowers.
3. Plant height to 1.2 meters with 1 meter width.
4. Above average plant vigor.
5. Fully double, dark red-purple flower color.
6. Strong resistance to powdery mildew.
7. Green foliage with distinctive bluish tinge.
8. Twiggy, shrubby growth habit.

PARENTAL COMPARISON

Plants of the new cultivar 'GRAppl' are similar to the unnamed seed parent in most horticultural characteristics. However, 'GRAppl' differs in the following:

1. Parent variety flower color is pink, whereas the new variety has red-purple flowers.
2. Flowers of the new variety are larger with more petals.
3. Foliage of the new variety is larger than the seed parent.
4. Flowers of the new variety are more fragrant.

Plants of the new cultivar 'GRAppl' are similar to the pollen parent in most horticultural characteristics. However, 'GRAppl' differs in the following:

1. New variety has a more rounded petal shape.
2. Plants of the new variety are denser, with more twiggy growth and more foliage.
3. Flowers of the new variety are a darker red-purple, with more purple coloration than the pollen parent.

COMMERCIAL COMPARISON

Of the many Rose varieties commercially available, plants of the new cultivar 'GRAppl' can be compared to the unpatented commercial variety *Rosa* hybrid 'Delviola'. 'GRAppl' differs from 'Delviola' in the following:

1. New variety has a deeper purple flower color.
2. Plants of the new variety are denser, with more twiggy growth and more foliage.
3. Plants of the new variety grow in a more upright habit.
4. Plants of the new variety are completely resistance to blackspot.

Plants of the new cultivar 'GRAppl' can be compared to the commercial variety *Rosa* hybrid 'Mackati', U.S. Plant Pat. No. 10,698. 'GRAppl' differs from 'Mackati' in the following:

1. New variety has a deeper purple flower color.
2. Plants of the new variety are denser, with more twiggy growth and more foliage.
3. Plants of the new variety grow in a more upright habit.
4. Plants of the new variety are completely resistance to blackspot.

BRIEF DESCRIPTION OF THE PHOTOGRAPHS

The accompanying photograph in FIG. 1 illustrates in full color a typical flower of 'GRAppl' grown outdoors in Highfields Australia.

Figure 2:
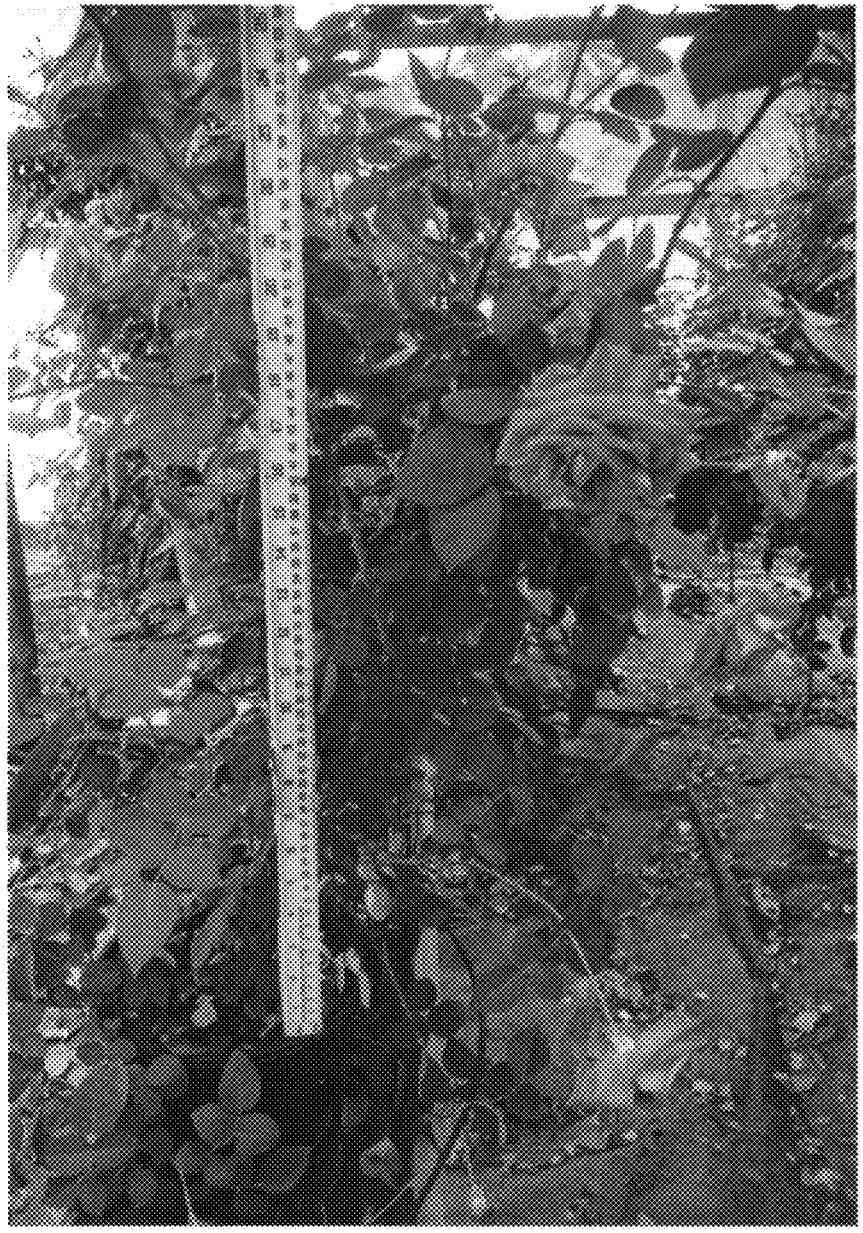

FIG. 2 illustrates in full color a typical plant of 'GRAppl' grown outdoors in Highfields Australia. The plant is approximately 12 months old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995, except where general terms of ordinary dictionary significance are used. The following observations and measurements describe 'GRAppl' plants grown in Clyde, Victoria, Australia, described during the Fall. Plants were grown in 20 cm containers in a soilless pine bark media, inside an open polythene covered greenhouse, with 70% shade. Ventilation was very good, plant nutrition was by liquid feed from a hydroponic solution designed for roses as required, generally every 1-2 days. The growing temperature ranged from 8° C. to 14° C. at night to 18° C. to 23° C. during the day. From the initial eye, the first generation was cut 10-20 cm. The second generation was allowed to flower with the lateral shoots (third generation) being left to flower from which the observations were made. No artificial light, photoperiodic treatments or chemical treatments were given to the plants. Measurements and numerical values represent averages of typical flowering types.

Botanical classification: *Rosa* hybrid 'GRAppl'.

Age of the plant described: Approximately 6 months.

Container size of the plant described: 20 cm commercial container.

PROPAGATION

Typical method: Vegetative cuttings.

Time to initiate roots: About 13 days at approximately 21° C. (rootzone) and 18° C. (average ambient).

Time to produce a rooted cutting: About 25 days at approximately 21° C. (rootzone) & 18° C. (average ambient).

Root description: Well branched, fibrous with many root hairs extending from lesser roots in a feather like arrangement. White coloration, not accurately measured with R.H.S. chart.

PLANT

Growth habit: Upright to semi-weeping.

Age of plant described: 6 months.

In a container or in the ground: Container.

Height: 85 cm.

Plant spread: 50 cm.

Rootstock: Own Roots.

Branching characteristics: Numerous irregular branching from mature stems from bud eyes towards the apex of each shoot.

Length of primary lateral branches: Approximately 40-60 cm.

Diameter of lateral branches: Approximately 0.5 tapering to 0.3 cm.

Quantity of lateral branches: Numerous.

Branching arrangement: Irregular.

Branches-young wood:

*Diameter*.—Approximately 0.5 cm.

*Texture*.—Smooth with some prickle hairs ranging from nil to medium density per branch.

*Approximately density/quantity of thorns*.—Moderate.

*Color*.—Near RHS Green 137B.

Branches-old wood:

*Diameter*.—Approximately 0.7 cm after 1 year.

*Texture*.—Smooth.

*Approximately density/quantity of thorns*.—Medium density.

*Color*.—Near RHS Green 143D.

Thorn description:

*Average height*.—6 mm.

*Average length*.—10 mm.

*Shape*.—Slight concave angling downward.

*Color*.—Immature: near RHS Greyed-Red 178A. Mature: near RHS Gren 143A, flushed Greyed-Red 178A.

FOLIAGE

Leaf:

*Arrangement*.—Alternate, compound.

*Quantity*.—Approximately 7 per main branch.

*Average length*.—Approximately 13.5 cm.

*Average width*.—Approximately 8.5 cm.

Leaflets:

*Shape of blade*.—Ovate.

*Apex*.—Acuminate.

*Base*.—Rounded to cordate.

*Margin*.—Serrated.

*Texture of top surface*.—Smooth.

*Texture of bottom surface*.—Course with small thornlike projections along veins.

*Average length*.—Approximately 5.5 cm. (terminal leaflet).

*Average width*.—Approximately 4 cm. (terminal leaflet) .

*Leaf internode length*.—1.5 to 3 cm.

*Color*.—Young foliage upper side: Near RHS Green 137C. Young foliage under side: Near RHS Green 138B with some crimson anthocyanin coloration, closest to Red-Purple 59A. Mature foliage upper side: Near RHS Green 139A. Mature foliage under side: Near RHS Green 138B.

*Venation*.—Type: Pinnate. Venation color upper side: Near Green 138A. Venation color under side: Near Green 138D.

*Rachis*.—Average length between the terminal and the secondary leaflet pairs 17 mm. Rachis colored near RHS Green 137D.

*Petiole*.—Length: 1 to 2.5 cm. Width: 1 cm at widest part. Color: Near Green 137C. Texture: Mainly smooth with some prickle hairs. Other Distinguishing Characteristics: Initial part of petiole (first 1 cm) is 0.4 cm wide with two side extensions (opposite) running horizontal and ending in acuminate apices measuring 1 cm apart from apex to apex.

FLOWER

Natural flowering season: Nearly continuous flowering from October to June in the Southern Hemisphere.

Begins flowering after how many years/months: 6-8 weeks for the stem to grow and mature. Flowering occurs after stem matures. First flowers 6-8 weeks from cutting/budded eye to break.

Inflorescence type and habit: Irregular whorled, double.

Rate of flower opening: Approximately 10 days from bud to fully opened flower.

Flower longevity on plant: 9 days, after fully opened.

Inflorescence size:

*Diameter*.—Approximately 10 cm.

*Length*.—Approximately 3.6 cm. (Flower height) with flat lower profile, flattened convex upper profile.

Peduncle:

*Length*.—8 cm.

*Diameter*.—0.2 cm.

Petals:

*Petal arrangement*.—Loose, irregular whorl.

*Size*.—Length: 5 cm. Width: 4.2 cm.

*Shape*.—Rounded.

*Margin*.—Medium reflexing on outer petals.

*Apex*.—Rounded.

*Base*.—Obtuse.

*Petal quantity*.—22.

*Texture*.—Soft, velvety.

Color:

*Petals*.—When opening: Upper surface: Near RHS Red-Purple 67A. Lower surface: Near RHS Red-Purple 66A. Fully opened: Upper surface: Near RHS Red-Purple 74A. Lower surface: Near RHS Red-Purple 74C.

Bud:

*Shape*.—Ovate.

*Length*.—Approximately 3.3 cm.

*Diameter*.—Approximately 1.8 cm.

*Color*.—Near RHS Red-Purple 60A.

Sepals:

*Length*.—2.8 cm.

*Width*.—1.1 cm.

*Shape*.—Weak sepal extensions with 2-3 lateral extensions and single non-feathering apex.

*Color*.—Interior Surface: Near RHS Yellow-Green 144A. Exterior Surface: Near RHS Yellow-Green 144D.

*Texture*.—Soft, slightly felt-like.

Receptacle:

*Length*.—0.6 cm.

*Width*.—0.6 cm.

*Shape*.—Pitcher shaped.

*Color*.—Green, not accurately measured by R.H.S. chart.

Fragrance: Strong, citrus-like scent.

REPRODUCTIVE ORGANS

Stamens:

*Number*.—Approximately 100.

*Filament length*.—Approximately 1.5 cm.

*Filament color*.—Near RHS Red-Purple 65A.

Anthers:

*Length*.—0.1 cm.

*Shape*.—Narrow ovate.

*Color*.—Near RHS Yellow-Orange 18B.

*Pollen*.—Color: Yellow-Orange 18B. Quantity: Abundant.

Pistil:

*Number*.—Approximately 30.

*Length*.—Approximately 0.5 cm.

*Style*.—Length: Approximately 0.4 cm. Color: Near RHS Red-Purple 60A.

*Stigma*.—Shape: Rounded. Color: Near RHS Yellow-Orange 18B. Ovary Color: Near RHS Green-Yellow 1D.

OTHER CHARACTERISTICS

Seeds and fruits: Not observed at the time of description.

Disease/pest resistance: Excellent tolerance to fungal diseases, and complete resistance to *Diploecarpon rosae*. As typical of many *Rosa* hybrid varieties, flowers are susceptible to *Botrytis* at the end of the season. Typically average resistance to normal pests of *Rosa* hybrid garden plants.

Temperature tolerance: Very good heat tolerance.

What is claimed is:

1. A new and distinct cultivar of *Rosa* hybrid plant named 'GRAppl' as herein illustrated and described.

* * * * *